United States Patent [19]
Alband

[11] Patent Number: 6,036,942
[45] Date of Patent: *Mar. 14, 2000

[54] SEAL CONFIGURATION FOR AEROSOL CANISTER

[75] Inventor: Todd D. Alband, Eagan, Minn.

[73] Assignee: 3M Innovative Properties Company, St. Paul, Minn.

[*] Notice: This patent is subject to a terminal disclaimer.

[21] Appl. No.: 09/110,795

[22] Filed: Jul. 6, 1998

Related U.S. Application Data

[63] Continuation of application No. 08/361,719, Dec. 22, 1994, Pat. No. 5,775,321, which is a continuation of application No. 08/057,239, Apr. 30, 1993, abandoned.

[51] Int. Cl.⁷ .............................. A61K 9/12; B65D 83/00
[52] U.S. Cl. .................. 424/45; 128/200.23; 222/402.1; 424/46
[58] Field of Search ................... 128/200.23; 222/402.1, 222/402, 373, 402.2, 398, 394; 424/45, 46; 277/228, DIG. 6

[56] References Cited

U.S. PATENT DOCUMENTS

| | | |
|---|---|---|
| 3,137,416 | 6/1964 | Shepherd et al. . |
| 3,581,958 | 6/1971 | Meshberg . |
| 3,592,364 | 7/1971 | Thornton . |
| 3,727,806 | 4/1973 | Wilmont . |
| 3,738,542 | 6/1973 | Ruscitti . |
| 4,271,875 | 6/1981 | Meshberg . |
| 4,407,481 | 10/1983 | Bolton et al. . |
| 4,427,137 | 1/1984 | Dubini . |
| 4,597,512 | 7/1986 | Wilmot . |
| 4,744,495 | 5/1988 | Warby . |
| 5,190,029 | 3/1993 | Byron et al. . |
| 5,225,183 | 7/1993 | Purewal et al. . |
| 5,427,282 | 6/1995 | Greenleaf . |
| 5,775,321 | 7/1998 | Alband . |

FOREIGN PATENT DOCUMENTS

| | | |
|---|---|---|
| 34350/93 | 8/1993 | Australia . |
| 1400459 | 4/1965 | France . |
| 1484238 | 5/1967 | France . |
| 2543923 | 10/1984 | France . |
| 2738557 | 3/1997 | France . |
| 4110381 | of 1992 | Japan . |
| 358758 | 1/1962 | Switzerland . |
| 2049064 | 12/1980 | United Kingdom . |
| 92/11190 | 7/1992 | WIPO . |
| 93/22221 | 11/1993 | WIPO . |
| 97/09034 | 3/1997 | WIPO . |
| 97/18146 | 5/1997 | WIPO . |

Primary Examiner—Raj Bawa
Attorney, Agent, or Firm—Ted K. Ringsred; MarySusan Howard; Robert W. Sprague

[57] ABSTRACT

An aerosol canister for containing a medicinal aerosol formulation. The canister involves a vial body and a valve ferrule sealed by first and second sealing members to form a chamber that contains the medicinal aerosol formulation.

13 Claims, 3 Drawing Sheets

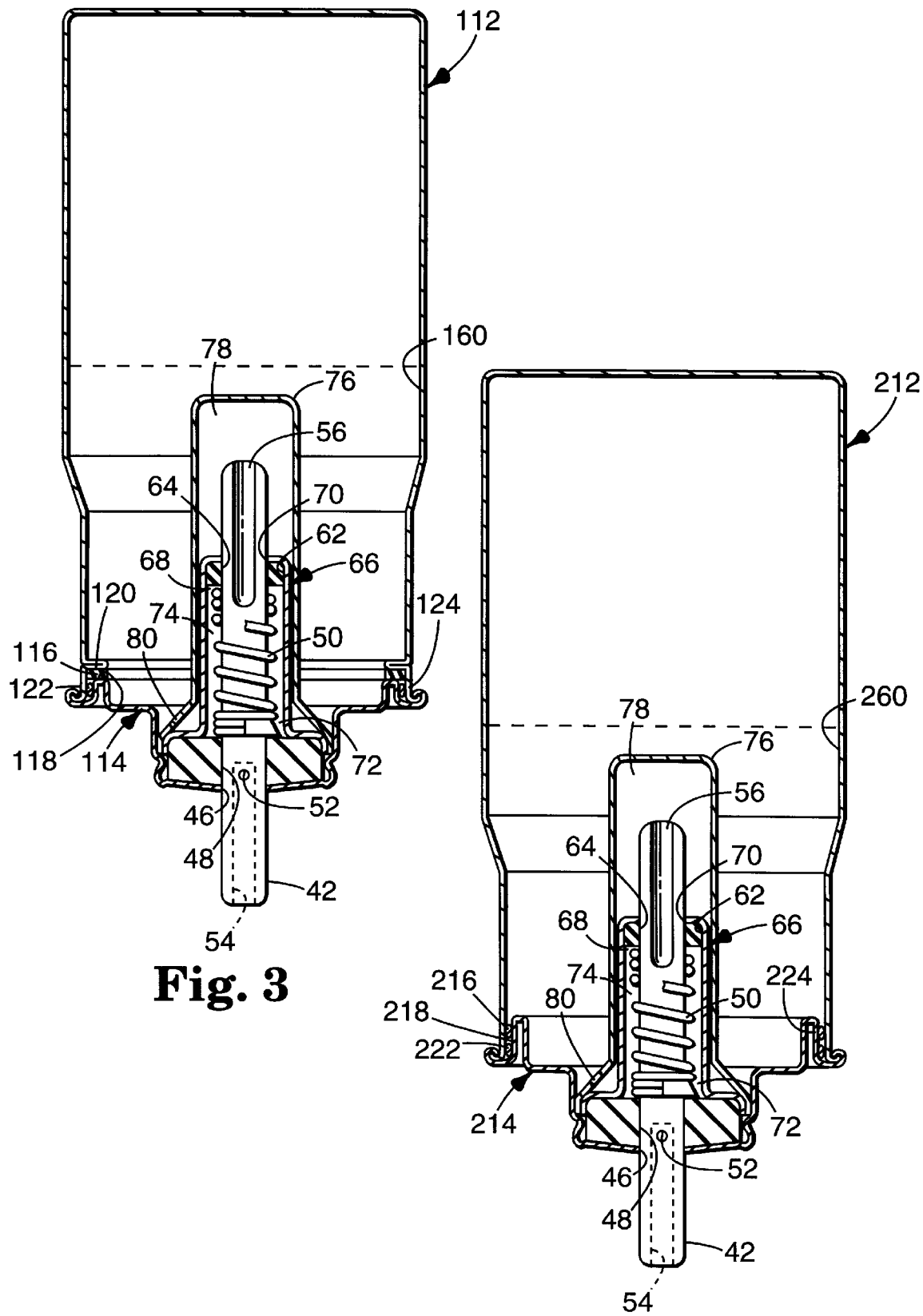

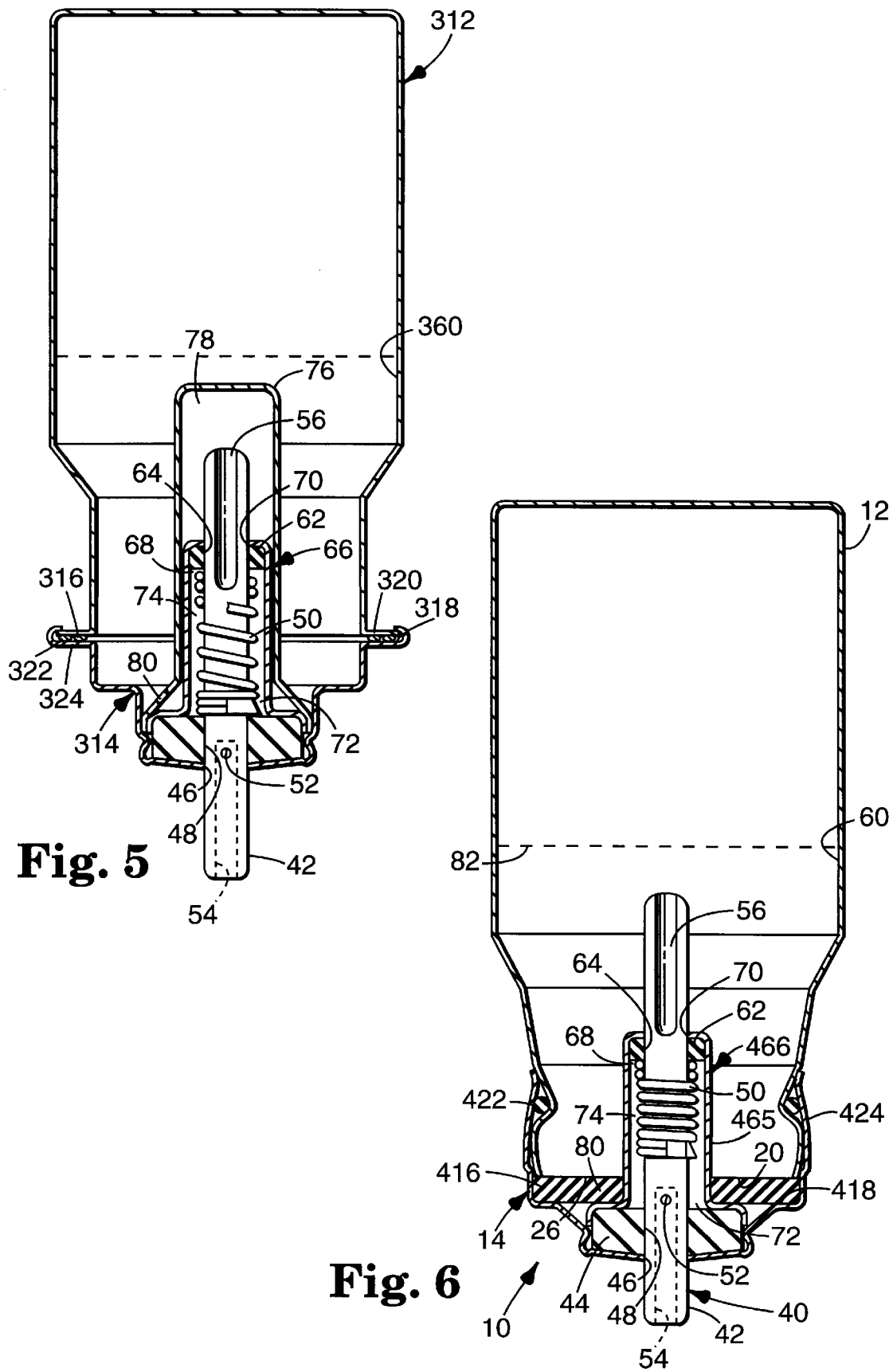

SEAL CONFIGURATION FOR AEROSOL CANISTER

This is a continuation of application Ser. No. 08/361,719 filed Dec. 22, 1994 U.S. Pat. No. 5,775,321 which is a continuation of application Ser. No. 08/057,239, filed Apr. 30, 1993, abandoned.

BACKGROUND OF THE INVENTION

1. Field of the Invention

This invention relates to canisters for containing medicinal aerosol formulations. In another aspect this invention relates to sealing members for use in such aerosol canisters. In yet another aspect this invention relates to methods of containing aerosol formulations involving 1,1,1,2-tetrafluoroethane as a propellant.

2. Description of the Related Art

Medicinal aerosol formulations are typically contained in a metal, plastic, or glass vial equipped with a metered dose valve. The valve typically is fitted to the body of the vial by crimping a valve ferrule against the body of the vial with an intermediate seal made of an elastomeric material compressed between the body and the ferrule. The intermediate seal can be in the form of a ferrule gasket placed and compressed between the top edge of the body of the vial and the opposing surface of the ferrule gasket, or it can be in the form of an o-ring placed around the body of the vial and compressed between the body of the vial and an annular flange of the valve ferrule.

Materials used as valve seals include BUNA rubbers, butyl rubbers, neoprene, and certain thermoplastic materials, such as those disclosed for such purpose in WO 92/11190 (Marecki). Medicinal aerosol formulations are sensitive to leakage of the propellant, perhaps more so than other aerosol formulations because of the need to maintain an appropriate concentration of the medicament. However, it is known that the suitability of valve seal materials for use in connection with medicinal aerosol formulations is dependent upon the propellant and other components used in the formulation (see, e.g., WO 92/11190 and WO 92/14444). As conventional propellants will soon be phased out of production, drugs for use in metered dose medicinal aerosols must be formulated using new propellants, such as 1,1,1,2-tetrafluoroethane, 1,1,1,2,3,3,3-heptafluoropropane, hydrocarbons, and the like. It is therefore necessary to devise sealing methods, materials, and vial configurations that allow long term storage of medicinal aerosol formulations based upon such alternative propellants.

SUMMARY OF THE INVENTION

This invention provides an aerosol canister for containing a medicinal aerosol formulation, comprising:

a vial body, a first seal, a second seal, and a valve ferrule, wherein the vial body has walls defining a vial opening, the valve ferrule occludes the vial opening and the vial body and the valve ferrule define a chamber, the first sealing member is disposed relatively nearer the chamber, the second sealing member is disposed relatively removed from the chamber, and the valve ferrule and vial body are in opposing sealing engagement with each of the sealing members.

The aerosol canister of the invention employs both first and second seals, e.g., a ferrule gasket or an o-ring and a second seal such as an o-ring, in order to reduce the rate of leakage of propellant from a medicinal aerosol formulation, particularly a formulation based on a propellant comprising a hydrofluorocarbon propellant (e.g., 1,1,1,2-tetrafluorethane) containing a polar cosolvent such as ethanol.

BRIEF DESCRIPTION OF THE DRAWING

In the Drawing like elements are given like reference numerals.

FIG. 3 shows a cross sectional view of an embodiment of the invention wherein the valve ferrule has a generally cylindrical flange extending along the interior of the vial body.

FIG. 4 shows a cross sectional view of an alternative embodiment of the invention wherein the valve ferrule has a generally cylindrical flange extending along the interior of the vial body.

FIG. 5 shows a cross sectional view of an embodiment of the invention wherein the valve ferrule and the vial body comprise complementary radial flanges.

FIG. 6 shows a cross sectional view of an embodiment of the invention wherein the first seal is a solution gasket.

DETAILED DESCRIPTION OF THE INVENTION

Figure 1:
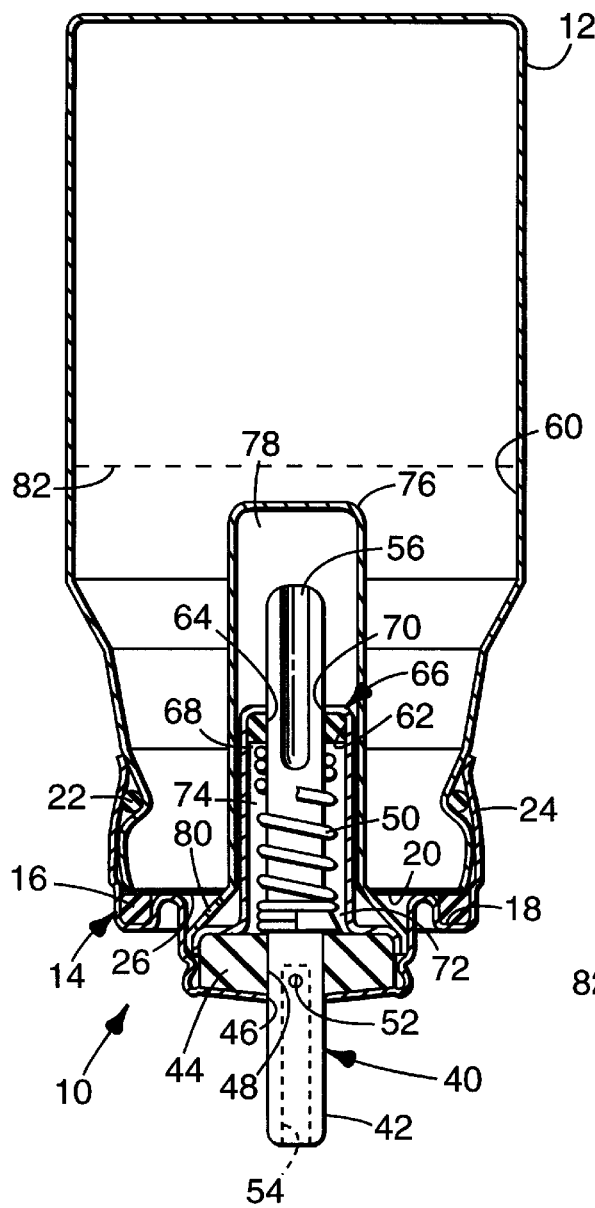
FIG. 1 shows a cross sectional view of a preferred embodiment of the aerosol canister of the invention having a metered dose valve in the extended closed position.

The invention involves a vial body and a valve ferrule that together can be assembled to form an aerosol canister. Any vial body useful in containing propellant based medicinal aerosol formulations be used, including conventional stainless steel, glass, and plastic (such as polyethylene terephthalate) vial bodies. Likewise the valve ferrule can be any valve assembly that can be fitted to the vial body and crimped or otherwise fixed into place to occlude the opening in the vial body. Suitable valve ferrules include any valve ferrule that can be used in connection with an aerosol vial body wherein the ferrule and vial body are constructed and arranged such that the ferrule and the vial body can be in opposing sealing engagement with each of the two sealing members as described below. Exemplary suitable ferrules include those that comprise a generally cylindrical skirt that extends along the exterior of the vial body, those that comprise a generally cylindrical skirt that extends along the interior of the vial body, and those that comprise a radial skirt that extends along a complementary radial skirt on the vial body. Valve ferrules comprising metered dose valve assemblies, such as those disclosed in U.S. Pat. No. 4,597,512 (Wilmot), U.S. Pat. No. 4,427,137 (Dubini), U.S. Pat. No. 4,407,481 (Botton et al.), U.S. Pat. No. 4,271,875 (Meshberg), and U.S. Pat. No. 3,738,542 (Ruscitti) are preferred.

The vial body and the valve ferrule define a chamber and are sealed with a dual seal combination comprising a first annular seal relatively nearer the chamber and a second annular seal relatively removed from the chamber. The first and second seals can be of the same configuration or different configuration. Any annular sealing member that has generally opposing surfaces, one of which can seal against a valve ferrule and the other of which can seal against a vial body, is suitable. Suitable cross sectional shape (e.g., rectangular, circular, elliptical, concavoconcave, etc.) of the first and second seals will depend on the configuration of the ferrule and the vial body and can be readily selected by those skilled in the art.

The first seal functions to seal the aerosol canister at or near the chamber. The first seal is preferably a ferrule gasket that seals against a gasket surface on the valve ferrule and against the vial body, preferably an annular rim on the vial body. The second seal is an annular seal such as an o-ring that functions to seal the aerosol canister in a region relatively further removed from the chamber (that is, in a region wherein the first seal is between the second seal and the chamber). Suitable second seals include those that seal against the vial body and against a valve ferrule skirt such as one that extends generally cylindrically along the exterior of the vial body, generally cylindrically along the interior of the vial body, or radially along a complementary skirt on the vial body.

The seals used in the aerosol canister of the invention can be composed of any conventional seal materials for use in containing medicinal aerosol formulations, including thermoset elastomers such as Buna rubbers (e.g., Buna-N), neoprene, and butyl rubbers, nitrile rubbers, and certain thermoplastic materials that have been shown to be useful as seals in medicinal aerosol canisters, such as thermoplastic elastomers comprising a copolymer of about 80 to about 95 percent ethylene and a total of about 5 percent to about 20 percent of one or more comonomers selected from the group consisting of 1-butene, 1-hexene, and 1-octene, including those disclosed in WO 92/11190 (Marecki). Exemplary thermoplastic elastomers of this class include:

FLEXOMER™ DFDA 1137 NT7 polyolefin (commercially available from Union Carbide), a thermoplastic elastomer comprising a copolymer of about 91 mole percent ethylene and about 9 mole percent 1-butene. This copolymer is said to have a density of 0.905 g/cm$^3$ (ASTM D-1505) and a melt index of 1.0 g/10 min (ASTM D-1238);

FLEXOMER™ DFDA 1138 NT polyolefin (commercially available from Union Carbide), a thermoplastic elastomer comprising a copolymer of about 91 mole percent ethylene and about 9 mole percent 1-butene and having a density of 0.900 g/cm$^3$ (ASTM D-1505) and a melt index of 0.4 g/10 min (ASTM D-1238);

FLEXOMER™ DFDA 1163 NT7 polyolefin (Union Carbide), comprising a copolymer of about 95 mole percent ethylene, about 1 mole percent 1-butene, and about 4 mole percent 1-hexene, having a density of 0.910 g/cm$^3$ (ASTM D 1238) and a melt index of about 0.5 g/10 min (ASTM D 1238);

FLEXOMER™ DFDA 1164 NT7 polyolefin (Union Carbide), comprising a copolymer of about 94 mole percent ethylene, about 1 mole percent 1-butene, and about 5 mole percent 1-hexene, having a density of about 0.910 g/cm$^3$ (ASTM D 1505) and a melt index of about 1.0 g/10 min (ASTM D 1238);

FLEXOMER™ 1491 NT7 polyolefin (Union Carbide), comprising a copolymer of about 90 mole percent ethylene and about 10 mole percent 1-butene, having a density of 0.900 g/cm$^3$ (ASTM D 1505) and a melt index of about 1.0 g/10 min (ASTM D 1238);

FLEXOMER™ 9020 NT7 polyolefin (Union Carbide), comprising a copolymer of about 92 mole percent ethylene and about 8 mole percent 1-butene, having a density of 0.905 g/cm$^3$ (ASTM D 1505) and a melt index of about 0.85 g/10 min (ASTM D 1238);

FLEXOMER™ 9042 NT polyolefin (Union Carbide), comprising a copolymer of about 80 mole percent ethylene and about 20 mole percent 1-butene, having a density of 0.900 g/cm$^3$ (ASTM D 1505) and a melt index of about 5.0 g/10 min (ASTM D 1238);

ATTANE™ 4602 polyolefin (Dow), comprising a copolymer of about 90 mole percent ethylene and about 10 mole percent 1-octene, having a density of 0.912 g/cm$^3$ (ASTM D 792) and a melt index of about 3.3 g/10 min,(ASTM D 1238);

ATTANE™ 4701 polyolefin (Dow), comprising a copolymer of about 92 mole percent ethylene and about 8 mole percent 1-octene, having a density of 0.912 g/cm$^3$ (ASTM D 792) and a melt index of about 1.0 g/10 min (ASTM D 1238).

Most preferred among these materials are FLEXOMER™ DFDA 1085 polyolefin and FLEXOMER™ DFDB 1085 polyolefin, each comprising a copolymer of about 80 mole percent ethylene and about 20 mole percent 1-butene, having a density of 0.884 g/cm$^3$ (ASTM D-1505) and a melt index of about 0.8 g/10 min (ASTM D 1238), and the latter comprising talc in an amount effective to reduce the tack of the polyolefin copolymer (Union Carbide).

Another class of thermoplastic elastomers is styrene-ethylene/butylene-styrene copolymer including those disclosed in commonly assigned copending application 07/878, 041 (Marecki). Such thermoplastic elastomers optionally further comprises a polyolefin, e.g., polypropylene, and further optionally comprises a siloxane such as polydimethylsiloxane or polymethyloctylsiloxane. These block copolymers preferably have a density between about 0.87 g/cm$^3$ and about 0.97 g/cm$^3$, more preferably between about 0.89 g/cm$^3$ and 0.91 g/cm$^3$. Shore A hardness is preferably between about 40 and about 95, more preferably between about 50 and about 75, and melt index is preferably about 0.3 g/10 min to about 3 g/10 min.

Certain suitable thermoplastic elastomers of this class are commercially available. Others can be prepared using methods known to those skilled in the art and disclosed, e.g., in U.S. Pat. Nos. 4,386,179, 4,481,323, and 4,511,354, all incorporated herein by reference. Preferred thermoplastic elastomers of this class include:

KRATON™ G rubbers (Shell Chemical Co., Houston, Tex.) such as KRATON G 1657 rubber.

C-FLEX™ thermoplastic elastomer R70-001 (Concept Polymer Technologies), a material comprising a styrene-ethylene/butylene-styrene (SEBS) block copolymer modified with polypropylene, dimethylsiloxane, and mineral oil, and having a density of 0.90 g/cm$^3$ and a melt index of 0.25 g/10 min.

C-FLEX™ thermoplastic elastomer R70-051, a material comprising a SEBS block copolymer modified with polypropylene, mineral oil, and polymethyloctylsilane as described in U.S. Pat. No. 4,613,640 (Deisler et al., the entire disclosure of which is incorporated herein by reference), having a density of 0.90 g/cm$^3$ and melt index of 2.7 g/10 min.

C-FLEX™ thermoplastic elastomer R70-041, a material comprising a SEBS block copolymer modified with polypropylene and polydimethylsiloxane having a density of 0.90 g/cm$^3$.

C-FLEX™ thermoplastic elastomer R70-085, a material comprising a SEBS block copolymer modified with polypropylene, mineral oil, and siloxanes including polymethyloctylsiloxane and having a density of 0.90 g/cm$^3$.

C-FLEX™ thermoplastic elastomer R70-003, a material comprising a SEBS block copolymer modified with polydimethylsiloxane, polypropylene, and mineral oil, having a density of 0.90 g/cm$^3$.

C-FLEX™ thermoplastic elastomer R70-026, a material comprising a SEBS block copolymer modified with polypropylene, polydimethylsiloxane, and mineral oil, having a density of 0.90 g/cm$^3$.

Such thermoplastic elastomers can also comprise minor amounts of conventional polymer additives such as processing aids, colorants, lubricants, silica, talc, or mineral oil.

Certain configurations of the dual seal combination are preferred. It is preferred that the first seal comprise a thermoplastic elastomer as described above. More preferably the first seal comprises a thermoplastic elastomer comprising a copolymer of about 80 to about 95 percent ethylene and a total of about 5 percent to about 20 percent of one or more comonomers selected from the group consisting of 1-butene, 1-hexene, and 1-octene, most preferably about 80 percent ethylene and about 20 percent 1-butene (e.g., Flexomer™ DFDB 1085).

The second seal preferably comprises a thermoset elastomer such as those enumerated above, most preferably Buna-N.

The preferred embodiment described above is particularly useful when used in connection with a medicinal aerosol formulation that uses HFC-134a as a propellant, and even more particularly when the formulation also contains ethanol.

In an embodiment wherein the first and second seals comprise different materials, it is preferred that the first and second seals be separate and distinct from one another as described and illustrated in connection with the Drawing. Also within the scope of the invention, however, are embodiments wherein the first and second seals are made of different materials and are integral with one another. For example the first and second seals can be in the form of a bilayered washer wherein one layer constitutes the first seal and the other layer constitutes the second seal. The seals can also be in the form of a coaxial o-ring having a core of one material and an exterior of another material. In such an embodiment the exterior would constitute the first seal and the core would constitute the second seal.

Figure 2:
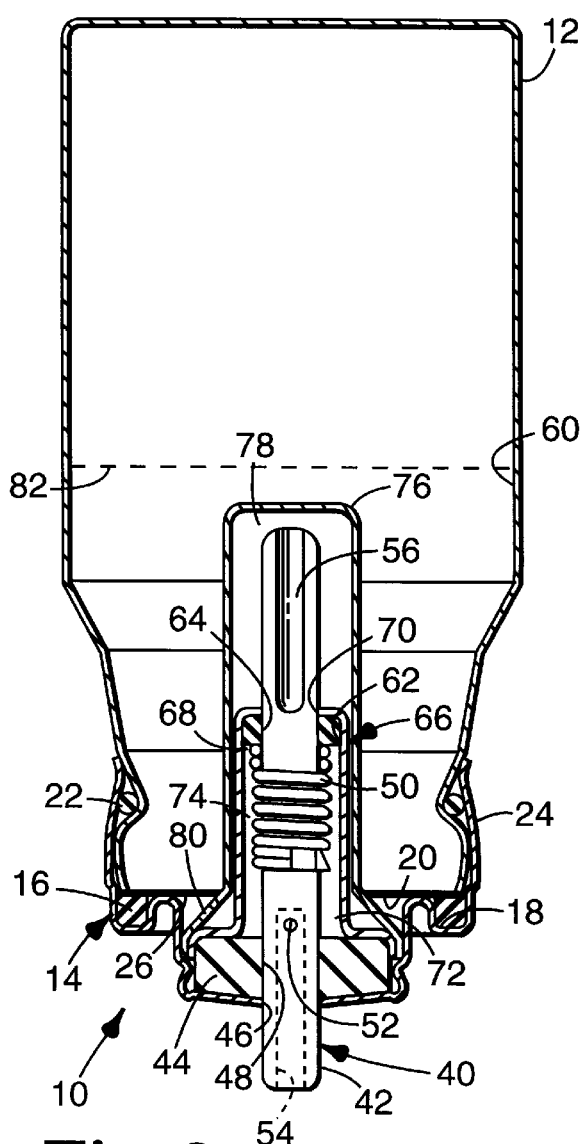
FIG. 2 shows a cross sectional view of the embodiment of FIG. 1, wherein the valve is in the compressed open position.

Referring now to FIGS. 1 and 2 of the Drawing, aerosol canister 10 comprises vial body 12 and valve ferrule 14. A first seal, represented by ferrule gasket 16, is in sealing engagement with gasket surface and with annular rim 20 of vial body 12. A second seal, represented by o-ring 22, is further removed from formulation chamber 60 and opening 26 in vial body 12 and is in sealing engagement with the exterior of vial body 12. O-ring 22 is also in sealing engagement with generally cylindrical skirt 24 of valve ferrule 14, which skirt extends along the exterior of vial body 12.

Valve ferrule 14 comprises a metered dose valve assembly 40. This valve assembly comprises valve stem 42 and diaphragm 44. The valve ferrule has walls defining ferrule aperture 46, and the diaphragm has walls defining diaphragm aperture 48. The valve stem passes through and is in slidable sealing engagement with the diaphragm aperture. The diaphragm is also in sealing engagement with the valve ferrule 14. Diaphragm dimensions can be easily selected by those skilled in the art.

Valve stem 42 is in slidable engagement with diaphragm aperture 48. Helical spring 50 holds the valve stem in an extended closed position as illustrated in FIG. 1. Valve stem 42 has walls defining orifice 52 which communicates with exit chamber 54 in the valve stem. The valve stem also has walls defining channel 56.

In the illustrated embodiment vial body 12 defines formulation chamber 60. The illustrated embodiment further comprises tank seal 62 having walls defining tank seal aperture 64, and metering tank 66 having inlet end 68, inlet aperture 70, and outlet end 72. The metering tank also has walls defining metering chamber 74 of predetermined volume (e.g., 50 µL). Outlet end 72 of metering tank 66 is in sealing engagement with diaphragm 44, and valve stem 42 passes through inlet aperture 70 and is in slidable engagement with tank seal 62.

Aerosol canister 10 further comprises optional retaining cup 76 fixed to valve ferrule 14 and having walls defining retention chamber 78 and aperture 80.

Operation of canister 10 is illustrated in FIGS. 1 and 2. In FIG. 1, the device is in the extended closed position. Aperture 80 allows open communication between retention chamber 78 and formulation chamber 60, thus allowing aerosol formulation 82 to enter the retention chamber. Channel 56 allows open communication between the retention chamber and metering chamber 74 thus allowing a predetermined amount of aerosol formulation to enter the metering chamber through inlet aperture 70. Diaphragm 44 seals outlet end 72 of the metering tank.

FIG. 2 shows canister 10 in the compressed open position. As valve stem 42 is depressed channel 56 is moved relative to tank seal 62 such that inlet aperture 70 and tank seal aperture 64 are substantially sealed, thus isolating a metered dose of formulation within metering chamber 74. Further depression of the valve stem causes orifice 52 to pass through ferrule aperture 46 and into the metering chamber, whereupon the metered dose is exposed to ambient pressure. Rapid vaporization of the propellant causes the metered dose to be forced through the orifice, and into and through exit chamber 54. Canister 10 is commonly used in combination with an actuator that facilitates inhalation of the resulting aerosol by a patient.

In FIGS. 3–5 components of the valve ferrule relating to the metered dose valve assembly are substantially as described above in connection with FIGS. 1 and 2.

Referring to FIG. 3, vial body 112 and valve ferrule 114 are sealed to define chamber 160 by a first seal 116 which is in sealing engagement with gasket surface 118 on the valve ferrule and with vial body 112 at annular rim 120. Second seal 122 is further removed from chamber 160 and is in sealing engagement with the interior of vial body 112 in a region relatively removed from chamber 160. Second seal 122 is also in sealing engagement with skirt 124, which extends along the interior of vial body 112.

Referring to FIG. 4, vial body 212 and valve ferrule 214 are sealed to define chamber 260 by a first seal 216, which is in sealing engagement with gasket surface 218 on the valve ferrule and vial body 212 in a region relatively near chamber 260. Second seal 222 is relatively removed from chamber 260 and is in sealing engagement with the interior of vial body 212. Second seal 222 is also in sealing engagement with skirt 224 which extends along the interior of vial body 212.

Referring to FIG. 5, vial body 312 and valve ferrule 314 are sealed to define chamber 360 by a first seal 316, which is in sealing engagement with gasket surface 318 of the valve ferrule and with vial body 312 in a region relatively near chamber 360. Second seal 322 is relatively removed from chamber 360 and is in sealing engagement with radial skirt 320 of vial body 312. Second seal 322 is also in sealing engagement with complementary radial skirt 324 of the valve ferrule.

FIG. 6 shows another embodiment of the invention having ferrule 414 substantially as illustrated in FIGS. 1 and 2 but not having an element corresponding to the optional retaining cup 76 shown, e.g., in FIGS. 1 and 2. Ferrule 414 has generally cylindrical skirt 424 extending along the exterior of vial body 412. First seal 416 is in the form of a washer-shaped solution gasket, which is in sealing engagement with gasket surface 418 and with annular rim 420 of vial body 412. First seal 416 also surrounds and is in sealing engagement with exterior 465 of metering tank 466 in order to protect the interior surface of the ferrule from contact with the formulation. The second seal, o-ring 422, is substantially as described above in connection with FIGS. 1 and 2.

A particularly preferred device of the invention is a metered dose device substantially as described above and illustrated in FIGS. 1 and 2. Other particular configurations, metered dose or otherwise, are well known to those skilled in the art are suitable for use with the dual seal combination of this invention.

Medicinal aerosol formulations generally contain the medicament, a propellant, and any necessary adjuvants and excipients (e.g., cosolvents, surfactants, and the like such as those disclosed in EP-A-372,777 Purewal et al., incorporated herein by reference). Depending on the particular formulation components and seal materials, the seal materials can be labile to the formulation components (e.g., reactive or unduly swellable). Accordingly it is preferred to select first and second seals such that the first seal provides an effective barrier to any formulation components to which the second seal is labile.

When a medicinal aerosol formulation (or a placebo formulation) is placed in an aerosol canister substantially as illustrated in FIGS. 1 and 2 and wherein the ferrule gasket comprises Flexomer™ DFDB 1085 polyolefin or another thermoplastic elastomer such as one of those enumerated above, and the o-ring comprises a Buna-N rubber or another thermoset elastomer known for use as a seal material, the leak rate is substantially reduced compared to the leak rate of a like canister absent the o-ring. This seal configuration finds particular utility in reducing leak rates when used in connection with a medicinal aerosol formulation involving a hydrofluorocarbon propellant, such as 1,1,1,2-tetrafluoroethane (HFC-134a) or 1,1,1,2,3,3,3-heptafluoropropane (HFC-227), and a polar cosolvent such as ethanol.

In the examples that follow the ferrule gaskets were all prepared from FLEXOMER™ DFDB 1085 polyolefin (Union Carbide), the o-rings (Buna-N rubber) were obtained from Parker Seal Group, Irvine, Calif., and the suspension aerosol formulation consisted of 0.385% micronized albuterol sulfate, 0.029% oleic acid, 14.440% ethanol and 85.146% 1,1,1,2-tetrafluoroethane with all percentages being by weight based on the total weight of the formulation.

After sealing all vials were stored at ambient conditions in an upright position for a two week quarantine period after which an initial weight was measured, the vials were then reweighed one week, three weeks, and six weeks after the initial weight was measured. The loss of mass over time was then extrapolated to one year and reported in mg/year.

EXAMPLE 1

Thirty 15 mL aluminum aerosol vials were each cold-filled with 7.6 g of the suspension formulation described above. All vials were then fitted using appropriate crimp settings with 25 µL valves equipped with diaphragms made from buna rubber (DB-218, American Gasket and Rubber, Chicago, Ill.). Ten of the vials (Lot A) were sealed using a gasket seal ferrule substantially as illustrated in FIGS. 1 and 2 and a ferrule gasket (no o-ring was used). Ten of the vials (Lot B) were sealed using a solution ferrule (a ferrule constructed and arranged in order to be sealed to an aerosol canister by way of an o-ring only) and an o-ring. Ten of the vials (Lot C) were sealed using a gasket seal ferrule (substantially as illustrated in FIGS. 1 and 2), a ferrule gasket, and an o-ring. Leak rate data for these three lots is shown in Table 1.

TABLE 1

| Lot | Seal(s) | Time (weeks) | Leak Rate (mg/yr) |
|---|---|---|---|
| A | ferrule gasket | 1 | 229 ± 9 |
|   |   | 3 | 222 ± 10 |
|   |   | 6 | 235 ± 10 |
| B | o-ring | 1 | 217 ± 16 |
|   |   | 3 | 243 ± 11 |
|   |   | 6 | 271 ± 13 |
| C | both | 1 | 133 ± 8 |
|   |   | 3 | 120 ± 8 |
|   |   | 6 | 136 ± 8 |

EXAMPLE 2

Thirty 15 mL aluminum aerosol vials were each cold-filled with 7.6 g of the suspension aerosol formulation described above. All vials were then fitted with 25 µL valves equipped with diaphragms made from FLEXOMER™ GERS 1085 polyolefin (Union Carbide). Ten of the vials (Lot D) were sealed using a gasket seal ferrule (substantially as illustrated in FIGS. 1 and 2) and a ferrule gasket (no o-ring was used). Ten of the vials (Lot E) were sealed using a solution ferrule and an o-ring. Ten of the vials (Lot F) were sealed using a gasket seal ferrule (substantially as illustrated in FIGS. 1 and 2), a ferrule gasket, and an o-ring. Leak rate data for these three lots is shown in Table 2.

TABLE 2

| Lot | Seal(s) | Time (weeks) | Leak Rate (mg/yr) |
|---|---|---|---|
| D | ferrule gasket | 1 | 132 ± 8 |
|   |   | 3 | 120 ± 11 |
|   |   | 6 | 135 ± 10 |
| E | o-ring | 1 | 112 ± 12 |
|   |   | 3 | 128 ± 9 |
|   |   | 6 | 157 ± 10 |
| F | both | 1 | 71 ± 45 |
|   |   | 3 | 67 ± 65 |
|   |   | 6 | 88 ± 72 |

EXAMPLE 3

Thirty 15 mL aluminum aerosol vials were each cold-filled with 7.6 g of the suspension aerosol formulation described above. Ten of the vials (Lot G) were sealed using a blind gasket seal ferrule (substantially as illustrated in FIGS. 1 and 2 but having no associated valve assembly 40 or ferrule aperture 46) and a ferrule gasket (no o-ring was used). Ten of the vials (Lot H) were sealed using a blind solution ferrule and an o-ring. Ten of the vials (Lot I) were sealed using a blind gasket ferrule, a ferrule gasket, and an o-ring. For all thirty vials, a metering tank was crimped to the ferrule prior to the ferrule being crimped onto the vial. Leak rate data for these three lots is shown in Table 3.

TABLE 3

| Lot | Seal(s) | Time (weeks) | Leak Rate (mg/year) |
|---|---|---|---|
| G | ferrule gasket | 1 | 132 ± 10 |
|   |   | 3 | 130 ± 9 |
|   |   | 6 | 141 ± 9 |
| H | o-ring | 1 | 135 ± 8 |
|   |   | 3 | 170 ± 7 |
|   |   | 6 | 201 ± 8 |
| I | both | 1 | 5 ± 5 |
|   |   | 3 | −2 ± 2 |
|   |   | 6 | 10 ± 2 |

The results in Tables 1–3 show that the exemplified aerosol canisters of the invention involving a ferrule gasket and an o-ring (Lots C, F, and I) have lower leak rates than the comparative examples having only a single seal. The canisters involving only an o-ring seal (Lots B, E, and H) show an increasing leak rate over time, thought to be due to the effect of ethanol on the o-ring seal.

I claim:

1. An aerosol canister containing a medicinal aerosol formulation, comprising:

a vial body, a first seal, a second seal, and a valve ferrule comprising a metered dose valve, wherein the vial body has walls defining a vial opening, the valve ferrule occludes the vial opening and the vial body and the valve ferrule define a chamber, the first sealing member is disposed relatively nearer the chamber, the second sealing member is disposed relatively removed from the chamber, and the valve ferrule and vial body are in opposing sealing engagement with each of the sealing; members and wherein the medicinal aerosol formulation comprises a propellant comprising 1,1,1,2-tetrafluoroethane or 1,1,1,2,3,3,3-heptafluoropropane.

2. An aerosol canister according to claim 1, wherein the first seal comprises a thermoplastic elastomer comprising a copolymer of about 80 to about 95 percent ethylene and a total of about 5 percent to about 20 percent of one or more comonomers selected from the group consisting of 1-butene, 1-hexene, and 1-octene.

3. An aerosol canister according to claim 2, wherein the first seal further comprises talc in an amount effective to reduce and/or eliminate tack.

4. An aerosol canister according to claim 1, wherein the first seal comprises a styrene-ethylene/butylene-styrene copolymer.

5. An aerosol canister according to claim 1, wherein the second seal comprises Buna rubber, neoprene, butyl rubber, or nitrile rubber.

6. An aerosol canister according to claim 1, wherein the medicinal aerosol formulation further comprises ethanol.

7. An aerosol canister according to claim 1, wherein the first seal comprises a thermoplastic elastomer comprising a copolymer of about 80 to about 95 percent ethylene and a total of about 5 percent to about 20 percent of one or more comonomers selected from the group consisting of 1-butene, 1-hexene, and 1-ocetene, or a thermoplastic elastomer comprising a styrene-ethylene/butylene-styrene copolymer, and the second seal comprises Buna rubber, neoprene, butyl rubber, or nitrile rubber, and wherein the first seal and the second seal are integral with one another.

8. An aerosol canister containing a medicinal aerosol formulation, comprising:

a generally cylinidrical vial body having exterior wall and an annular rim defining an opening, a valve ferrule comprising a metered dose valve and having an annular gasket surface and a generally cylindrical flange, a ferrule gasket, and an o-ring seal, wherein The gasket surface of the valve ferrule and the annular rim of the vial body are in opposing sealing engagement with the ferrule gasket, and the valve ferrule occludes the opening in the vial body to define a chamber, The flange of the valve ferrule extends along the exterior wall of the vial body, and the vial body and the flange are in opposing sealing engagement with the o-ring; and Wherein the medicinal aerosol formulation comprises a propellant comprising 1,1,1,2-tetrafluoroethane or 1,1,1,2,3,3,3-heptafluoroproane.

9. An aerosol canister according to claim 8, wherein the first seal comprises a thermoplastic elastomer comprising a copolymer of about 80 to about 95 percent ethylene and a total of about 5 percent to about 20 percent of one or more comonomers selected from the group consisting of 1-butene, 1-hexene, and 1-octene.

10. An aerosol canister according to claim 9, wherein the first seal further comprises talc in an amount effective to reduce and/or eliminate tack.

11. An aerosol canister according to claim 8, wherein the first seal comprises a styrene-ethylene/butylene-styrene copolymer.

12. An aerosol canister according to claim 8, wherein the second seal comprises a Buna rubber.

13. An aerosol canister according to claim 8, wherein the medicinal aerosol formulation further comprises ethanol.

* * * * *

UNITED STATES PATENT AND TRADEMARK OFFICE
CERTIFICATE OF CORRECTION

PATENT NO. : 6,036,942
DATED : March 14, 2000
INVENTOR(S) : Todd D. Alband

It is certified that error appears in the above-identified patent and that said Letters Patent is hereby corrected as shown below:

Column 9,
Line 34, delete the semicolon (;) after the word sealing.

Signed and Sealed this

Second Day of April, 2002

Attest:

Attesting Officer

JAMES E. ROGAN
Director of the United States Patent and Trademark Office